United States Patent
Yao et al.

(10) Patent No.: US 8,432,544 B2
(45) Date of Patent: Apr. 30, 2013

(54) METHOD FOR DETECTING BPA BY SURFACE ENHANCED RAMAN SPECTROSCOPY

(75) Inventors: Weirong Yao, Wuxi (CN); Shitao Wang, Wuxi (CN); Heya Wang, Wuxi (CN)

(73) Assignee: Jiangnan University, Wuxi, Jiangsu Province (CN)

( * ) Notice: Subject to any disclaimer, the term of this patent is extended or adjusted under 35 U.S.C. 154(b) by 13 days.

(21) Appl. No.: 13/376,998

(22) PCT Filed: Feb. 15, 2011

(86) PCT No.: PCT/CN2011/000234
§ 371 (c)(1),
(2), (4) Date: Dec. 8, 2011

(87) PCT Pub. No.: WO2012/040990
PCT Pub. Date: Apr. 5, 2012

(65) Prior Publication Data
US 2012/0236300 A1    Sep. 20, 2012

(30) Foreign Application Priority Data

Sep. 29, 2010   (CN) .......................... 2010 1 0295960

(51) Int. Cl.
*G01J 3/44*    (2006.01)
*C07C 37/68*   (2006.01)
(52) U.S. Cl.
USPC .......................................... 356/301; 568/724
(58) Field of Classification Search .......... 356/301–318; 568/724
See application file for complete search history.

(56) References Cited

U.S. PATENT DOCUMENTS

| | | | |
|---|---|---|---|
| 4,166,899 A * | 9/1979 | Maruyama et al. | 528/480 |
| 6,558,624 B1 * | 5/2003 | Lemmon et al. | 422/69 |
| 2003/0100686 A1 * | 5/2003 | Hu et al. | 525/443 |
| 2007/0020144 A1 * | 1/2007 | Du et al. | 422/58 |
| 2008/0202195 A1 * | 8/2008 | Joo et al. | 73/1.02 |
| 2010/0300883 A1 * | 12/2010 | Peterman | 204/600 |

FOREIGN PATENT DOCUMENTS

| | | |
|---|---|---|
| CN | 101661021 A | 3/2010 |
| CN | 101701944 A | 5/2010 |
| CN | 101776604 A | 7/2010 |
| JP | 61021128 * | 1/1986 |
| JP | 2004331916 A | 11/2004 |
| WO | WO-02/33388 A1 | 4/2002 |

\* cited by examiner

*Primary Examiner* — Tarifur Chowdhury
*Assistant Examiner* — Sunghee Y Gray
(74) *Attorney, Agent, or Firm* — Muncy, Geissler, Olds & Lowe, PLLC

(57) ABSTRACT

A detection method of bisphenol A by the surface-enhanced Raman spectroscopy includes: soaking and extracting bisphenol A present in a sample with an organic solvent to form an extraction solution, adding methanol to the extraction solution to cause a polymer to precipitate from the extraction solution and leaving a filtrate behind, filtering and concentrating the filtrate, diluting the concentrated filtrate to volume with methanol, filtering the diluted filtrate through a filter with a pore size of 0.45 μm to obtain a pretreated sample; detecting bisphenol A present in the sample by Raman spectroscopy under an incident laser power of 100 to 300 mW, and a scan time of 2 to 20 seconds; mixing the pretreated sample with the colloidal gold in an appropriate ratio, followed by adjusting pH value, and then carrying out the detection of bisphenol A present in the sample by Raman spectroscopy.

4 Claims, 3 Drawing Sheets

METHOD FOR DETECTING BPA BY SURFACE ENHANCED RAMAN SPECTROSCOPY

BACKGROUND OF THE INVENTION

1. Field of the Invention

The present invention relates to a method for detecting bisphenol A present in the plastic packing material as plasticizer, and particularly relates to a method for detecting bisphenol A by surface enhanced Raman spectroscopy.

2. The Prior Arts

Bisphenol A (BPA) is an important organic material that is primarily used to make polycarbonate plastics and epoxy resins, polysulfone resins, poly(phenylene ether) resins, and unsaturated polyester resins, and these polymers are used in many food and drink packaging applications. Therefore, bisphenol A is widely used in our daily life. The scientists found that Bisphenol A mimics estrogenic activity in 1938, and is regarded as an environmental oestrogen. When bisphenol A enters the body, it can cause an oestrogen-like effect, and consequently, even in the low dose, bisphenol A can cause issues, such as premature adolesence, reduction in sperm counts, and prostatic hyperplasia. Migration of bisphenol A shall not exceed 3 mg/kg, as regulated in directive 2002/72/EC of the European Communities. In October 2008, the government of Canada declared bisphenol A was acted as a toxic substance. In February 2009, bisphenol A was banned from use in baby bottles, water bottles, and the like in Canada. Then, in May 2009, bisphenol A was banned from use in the products in the states of Minnesota and Connecticut in the USA.

Many detection methods for determining the concentrations of bisphenol A have been developed, the primary of which are GC/MS, HPLC/MS, enzyme-linked immunosorbent assay (ELISA) methods, but, however, in these conventional detection methods of bisphenol A, the operation is complicated, and the analyzing time is long. Therefore, the present invention provides a detection method of bisphenol A by surface-enhanced Raman spectroscopy, which makes it possible to simply and quickly analyze the concentrations of bisphenol A. Furthermore, there are no reports on the detection method of bisphenol A by surface-enhanced Raman spectroscopy so far.

BRIEF DESCRIPTION OF THE DRAWINGS

The present invention will be apparent to those skilled in the art by reading the following detailed description of the preferred embodiments thereof, with reference to the attached drawings, in which.

SUMMARY OF THE INVENTION

Figure 1:
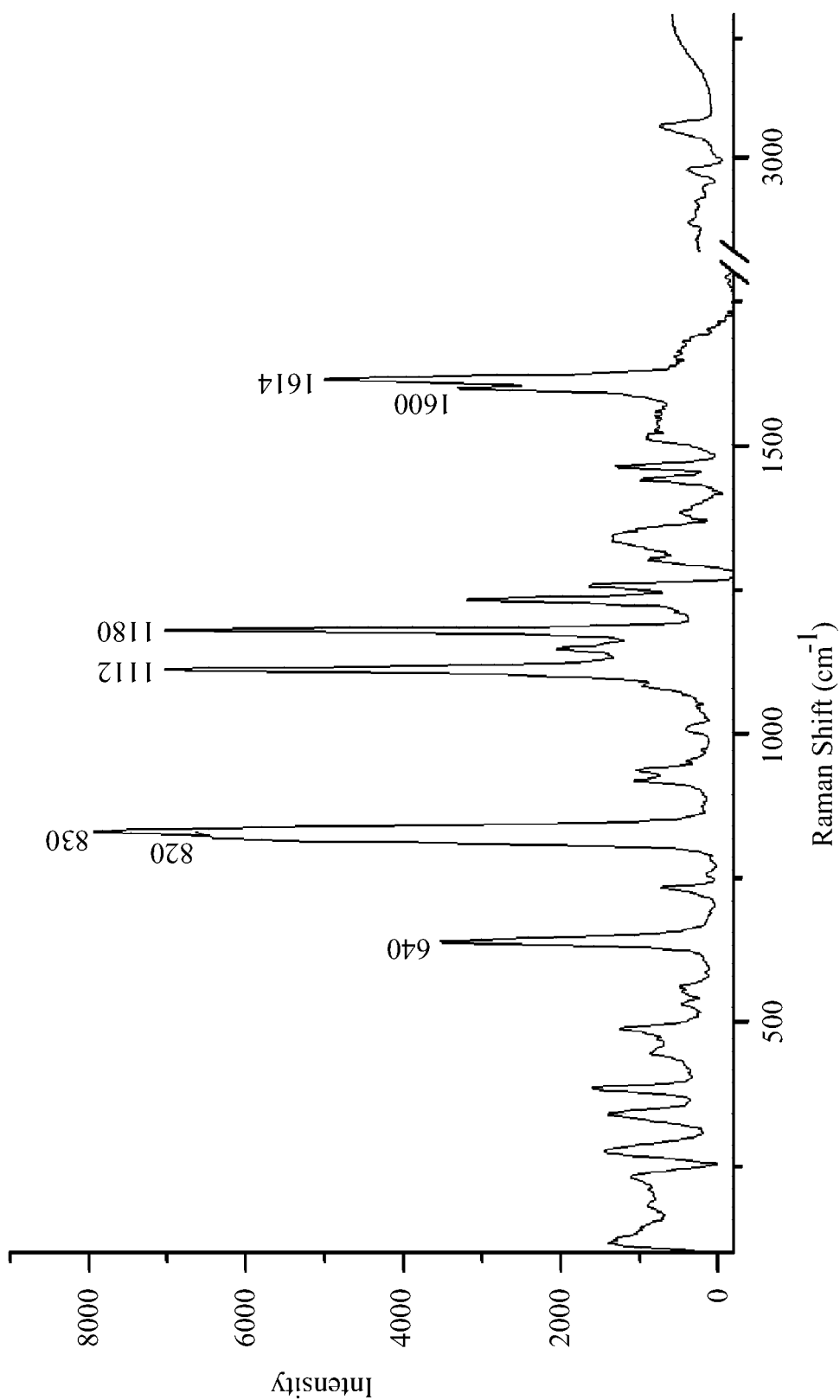
FIG. 1 is a Raman spectrum of bisphenol A.
Figure 2:
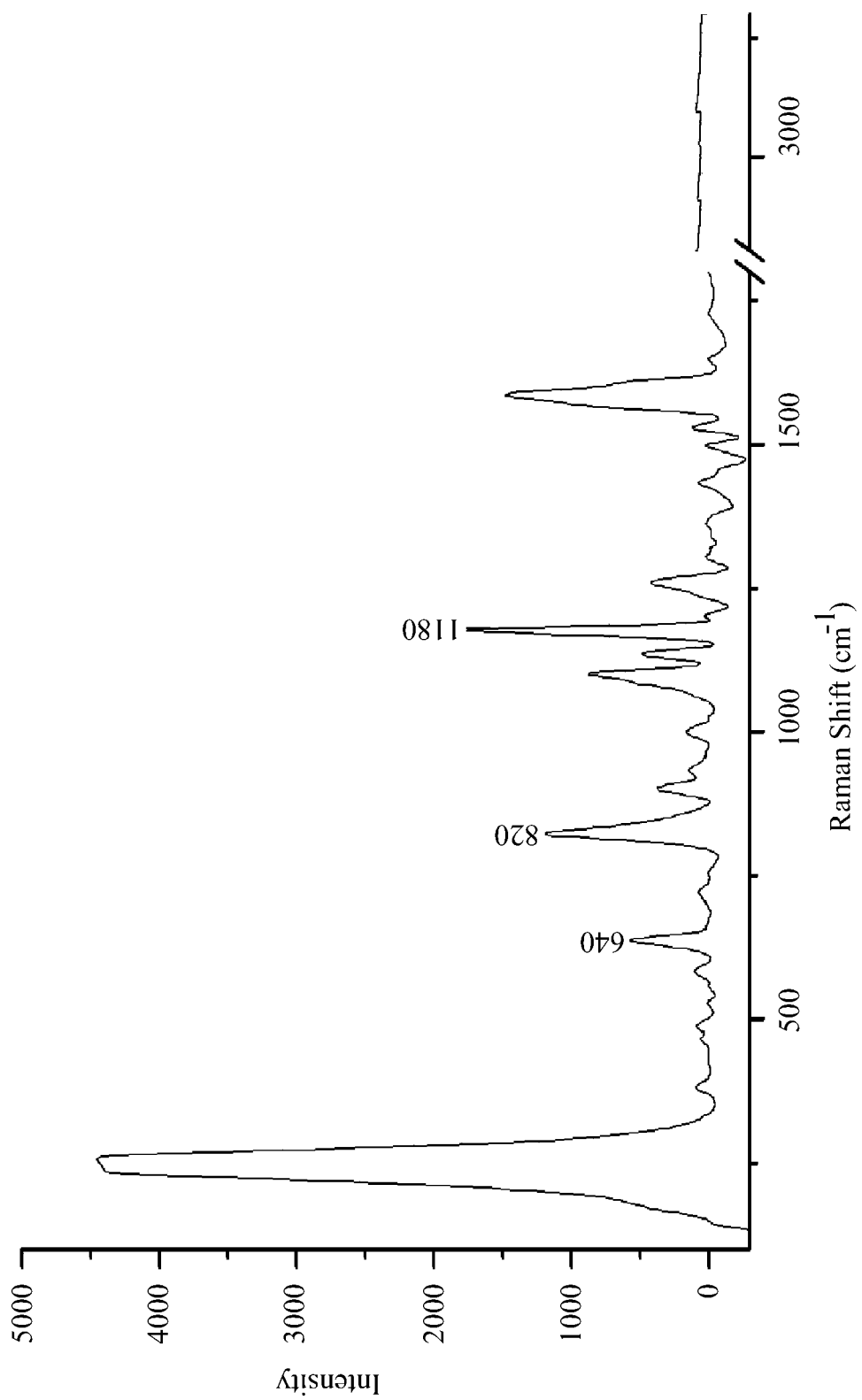
FIG. 2 is a surface-enhanced Raman spectrum of bisphenol A.

Accordingly, an objective of the present invention is to provide a detection method of bisphenol A by surface-enhanced Raman spectroscopy, so that the concentration of bisphenol A can be simply and rapidly analyzed.

In order to achieve the above objective, the present invention provides a detection method of bisphenol A by surface-enhanced Raman spectroscopy as follows:

(1) Sample Pretreatment

The extraction solvent is rapidly injected into the container containing the sample, and then the container is sealed, followed by ultrasound extraction until the sample therein is completely dissolved. Then, methanol is added to the container containing the dissolved sample to cause the polymer to precipitate from the extraction solution, and then the filtrate is filtered and concentrated, and subsequently the concentrated filtrate is diluted to volume with methanol, followed by filtering the diluted filtrate through a filter with a pore size of 0.45 μm for use in the Raman spectroscopy experiment.

(2) Preparation of Colloidal Gold

Powders of $KAuCl_4$ are precisely weighted, followed by dissolving the powders of $KAuCl_4$ in an ultrapure water to form a solution, boiling the solution with stirring, and then rapidly adding a sodium citrate solution thereto with stirring for 20 to 40 minutes. Then, the resulting solution is cooled to room temperature so as to obtain the colloidal gold for use.

(3) Spectral Conditions for Raman Spectroscopy 100 to 300 mW of incident laser power is used, and the scan time is 2 to 20 seconds.

(4) Standard Curve for the Determination of the Concentration of Bisphenol A is Drawn Based on the Raman Spectroscopy and the Surface-Enhanced Raman Spectroscopy A certain amount of powders of bisphenol A is weighted, and evenly pulverized. Then, the pulverized powders of bisphenol A are used as a sample in Raman spectroscopy. Then, 1.0 mg of bisphenol A is precisely weighted, followed by dissolving the bisphenol A in an appropriate amount of methanol to form a solution, and then transferring the solution to a 100 ml of volumetric flask and diluting to volume with methanol. Then, the volumetric flask containing bisphenol A dissolved in methanol is shaken, and let it to stand to obtain the standard solution of bisphenol A. Subsequently, the standard solution of bisphenol A is step-by-step diluted to the concentrations of 0.1, 0.5, 1.0, 2.0, and 5.0 μg/ml, respectively. The 0.1, 0.5, 1.0, 2.0, and 5.0 μg/ml of the bisphenol A solutions are respectively mixed with colloidal gold prepared in (2) in an appropriate ratio, and then $HNO_3$ is respectively added to each resulting mixture to adjust the pH value thereof using an acid or a base, wherein the acid can be $HNO_3$, HCL, $H_2SO_4$, or $H_3PO_4$ solution, and the base can be NaOH solution, and subsequently the Raman measurements are carried out by using each resulting mixture as sample in accordance with the spectral conditions for Raman spectroscopy described in (3). The standard curve for the determination of the concentration of bisphenol A is then drawn in a coordinate system using bisphenol A concentration (μg/ml) as the abscissa and the peak height of the characteristic peak of bisphenol A as the ordinate.

(5) Determination of the Concentration of Bisphenol A in a Sample

The sample is pretreated according to sample pretreatment described in (1), and then the surface enhanced Raman spectroscopy study described in (4) is carried out on the pretreated sample.

The advantages of the present invention are that the low level concentration of bisphenol A present in a packing material can be easily, rapidly and precisely determined at low cost by using the detection method of the present invention. Therefore, the large amounts of samples can be detected by the detection method used in the present invention. Therefore, the detection method of bisphenol A by surface-enhanced Raman spectroscopy used in the present invention can be standardized.

DETAILED DESCRIPTION OF THE PREFERRED EMBODIMENT

Hereinafter, the preferred embodiments of the present invention will be described in detail with reference to the accompanying drawings.

Example 1

Figure 3:
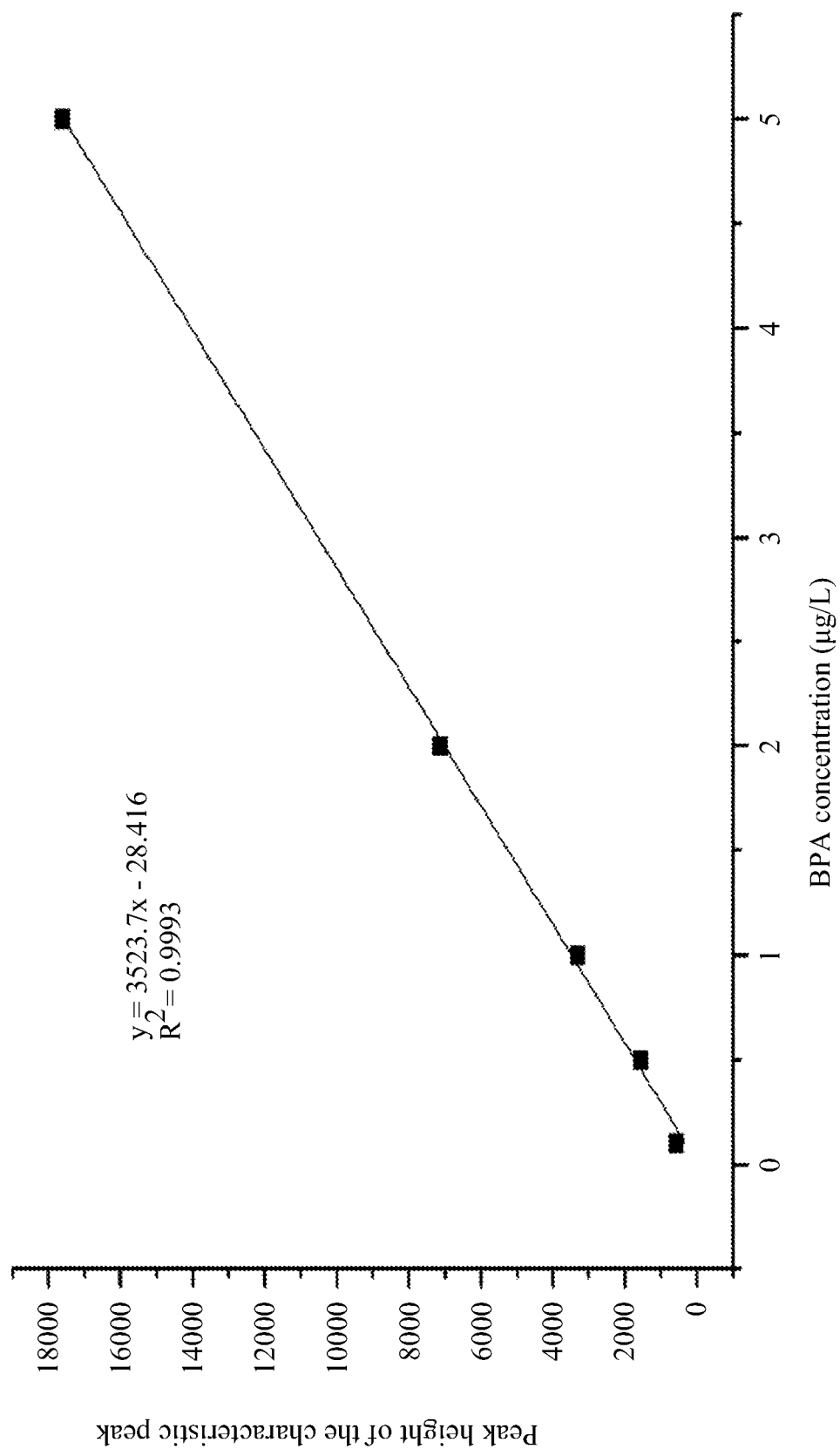
FIG. 3 is a standard curve for the determination of the concentration of bisphenol A in a coordinate system using bisphenol A concentration as the abscissa and the peak height of the 1180 $cm^{-1}$ peak of bisphenol A as the ordinate in accordance with one embodiment of the present invention.

1.0 mg of bisphenol A is precisely weighted, followed by dissolving the bisphenol A in an appropriate amount of methanol to form a solution, and then transferring the solution to a 100 ml of volumetric flask and diluting to volume with methanol. Then, the volumetric flask containing bisphenol A dissolved in methanol is shaken, and let it to stand to obtain a 10 μg/ml standard solution of bisphenol A. Subsequently, the standard solution of bisphenol A is step-by-step diluted to the concentrations of 0.1, 0.5, 1.0, 2.0, and 5.0 μg/ml, respectively. The 20 μL of 0.1, 0.5, 1.0, 2.0, and 5.0 μg/ml of the bisphenol A solutions are respectively mixed with 500 μL of colloidal gold, and then 50 μL of 0.5 M of $HNO_3$ is respectively added to each resulting mixture to adjust the pH value thereof, and subsequently the Raman measurements are carried out by using each resulting mixture as sample. The standard curve for the determination of the concentration of bisphenol A is then drawn in a coordinate system using bisphenol A concentration as the abscissa and the peak height of the 1180 $cm^{-1}$ peak of bisphenol A as the ordinate (refer to FIG. 3). This yields a standard curve defined by the equation y=3523.7x−28.416, and related coefficient: $R^2$=0.9993. A straight line represented by this equation can be drawn, and thereby the concentration of bisphenol A present in the sample can be determined.

Example 2

The polycarbonate material is cut into pieces with the size of about 0.5 cm×0.5 cm. Then, 0.5 g of the pieces of the polycarbonate material is taken into a container containing 10 mL of trichloromethane, followed by an ultrasound extraction until the pieces of the polycarbonate material therein is completely dissolved. Then, methanol is added to the container containing the dissolved polycarbonate material so that the volume of the solution becomes 25 mL. Precipitation will occur after a while, and then the filtrate is filtered and dried out at 40° C. by rotational evaporation. Subsequently, methanol is added so that the volume of the filtrate becomes 2 mL. Then, the diluted filtrate is filtered through a filter with a pore size of 0.45 μm for use in the Raman spectroscopy experiment. Three parallel samples of the polycarbonate material are provided, i.e. parallel sample 1, parallel sample 2, and parallel sample 3, and the analytical results from the three parallel samples are presented in Table 1. The parallel sample 1 is repeatedly detected for six times, and the analytical results are presented in Table 2. The relative standard deviation (RSD) of the three parallel samples detected is 8.33%. The relative standard deviation of the parallel sample 1 repeatedly detected for six times is 6.09%, which has higher repeatability.

TABLE 1

|  | Sample No. | | |
| --- | --- | --- | --- |
|  | Parallel sample 1 | Parallel sample 2 | Parallel sample 3 |
| Concentrations of BPA present in the sample (μg/g) | 7.53 | 7.65 | 7.49 |
| Average value (μg/g) |  | 7.56 |  |
| Relative standard deviation (%) |  | 8.33 |  |

TABLE 2

| Number | 1 | 2 | 3 | 4 | 5 | 6 | Average value | RSD (%) |
| --- | --- | --- | --- | --- | --- | --- | --- | --- |
| Concentrations of BPA present in parallel sample 1 (μg/g) | 7.53 | 7.46 | 7.55 | 7.63 | 7.48 | 7.56 | 7.54 | 6.09 |

Example 3

The different amounts of the standard solution of bisphenol A are added to the polycarbonate material including the known concentration of bisphenol A. Afterwards, the same procedure as shown in Example 2 is followed. Each sample is repeatedly detected for six times. The recovery rate and the relative standard deviation for each sample are determined, and the analytical results are presented in Table 3. The recovery rate is in the range of 91.50% to 98.60%. The relative standard deviation is in the range of 2.42% to 4.50%.

TABLE 3

| Concentrations of BPA present in the sample (μg/g) | Addition amount (μg/g) | Measurement value (μg/g) | Recovery rate (%) | RSD (%) |
| --- | --- | --- | --- | --- |
| 7.50 | 4.00 | 11.19 | 93.17 | 2.42 |
| 7.50 | 8.00 | 15.38 | 98.60 | 3.97 |
| 7.50 | 15.00 | 21.20 | 91.50 | 4.50 |

What is claimed is:

1. A Method for detecting BPA by Surface Enhanced Raman Spectroscopy, comprising:
   (1) soaking and ultrasonically extracting bisphenol A present in a sample with an organic solvent to form an extraction solution, adding methanol to the extraction solution to cause a polymer to precipitate from the extraction solution and leaving a filtrate behind, filtering and concentrating the filtrate, diluting the concentrated filtrate to volume with methanol, and filtering the diluted filtrate through a filter with a pore size of 0.45 μm to obtain a pretreated sample;
   (2) reducing $KAuCl_4$ with sodium citrate to obtain colloidal gold with evenly-distributed particle sizes;
   (3) detecting bisphenol A present in the sample by Raman spectroscopy, wherein spectral conditions for Raman spectroscopy include an incident laser power of 100 to 300 mW, and a scan time of 2 to 20 seconds; and
   (4) mixing the pretreated sample obtained in step (1) with the colloidal gold obtained in step (2) in an appropriate ratio, followed by adjusting pH value with an acid or a base, and then carrying out the detection of bisphenol A present in the sample by Raman spectroscopy under the spectral conditions shown in step (3).

2. The method according to claim 1, wherein the organic solvent used in step (1) is one of dichloromethane and trichloromethane.

3. The method according to claim 1, wherein the acid used in step (4) is $HNO_3$, HCL, $H_2SO_4$, or $H_3PO_4$ solution, and the base used in step (4) is NaOH solution.

4. The method according to claim 1, wherein the acid used in step (4) is $HNO_3$ solution.

* * * * *